United States Patent
Hendrix et al.

(10) Patent No.: US 10,514,332 B1
(45) Date of Patent: Dec. 24, 2019

(54) SYSTEMS AND METHODS FOR PROVIDING A PROFILE OF A MATERIAL PROPERTY USING MULTIPLE ANALYSIS STATIONS

(71) Applicant: Micromeritics Instrument Corporation, Norcross, GA (US)

(72) Inventors: Preston Hendrix, Lawrenceville, GA (US); Samuel Varner, Lilburn, GA (US)

(73) Assignee: Micromeritics Instrument Corporation, Norcross, GA (US)

( * ) Notice: Subject to any disclaimer, the term of this patent is extended or adjusted under 35 U.S.C. 154(b) by 183 days.

(21) Appl. No.: 15/839,979

(22) Filed: Dec. 13, 2017

Related U.S. Application Data

(60) Provisional application No. 62/434,233, filed on Dec. 14, 2016.

(51) Int. Cl.
*G01N 15/08* (2006.01)
*G01N 1/22* (2006.01)

(52) U.S. Cl.
CPC ....... *G01N 15/0893* (2013.01); *G01N 1/2214* (2013.01); *G01N 15/0806* (2013.01)

(58) Field of Classification Search
CPC .............. G01N 15/0893; G01N 15/08; G01N 2015/0833; G01N 15/088
See application file for complete search history.

(56) References Cited

U.S. PATENT DOCUMENTS

| | | | | | |
|---|---|---|---|---|---|
| 2,692,497 | A | * | 10/1954 | Nordstrand | G01N 15/0893 73/19.05 |
| 2,729,969 | A | * | 1/1956 | Innes | G01N 15/0893 73/38 |
| 3,059,478 | A | * | 10/1962 | Coggeshall | G01N 15/0893 73/865.5 |
| 3,211,007 | A | * | 10/1965 | Atkins | G01N 15/0893 73/865.5 |
| 3,349,625 | A | * | 10/1967 | Benusa | G01N 30/00 73/865.5 |
| 3,464,273 | A | * | 9/1969 | Orr, Jr. | G01N 15/0893 73/865.5 |

(Continued)

OTHER PUBLICATIONS

Micromeritics 3Flex—Surface and Catalyst Characterization; High-Resoluton, Improved Throughput Micropore Analyses; Brochure# 350/42701/00; 2016.

(Continued)

*Primary Examiner* — David A Rogers
(74) *Attorney, Agent, or Firm* — Womble Bond Dickinson (US) LLP

(57) ABSTRACT

Systems and methods for profiling a material property are provided. A plurality of measurement devices can be configured to measure at least a portion of the material property. A controller including at least one processor can be in communication with one or more of the plurality of measurement devices. At least one measurement device of the plurality of measurement devices can measure at least one segment of the material property, and at least one additional measurement device of the plurality of measurement devices can measure at least one additional segment of the material property. The at least one segment and the at least one additional segment can be combined to provide at least a partial profile of the material property.

20 Claims, 8 Drawing Sheets

(56) References Cited

U.S. PATENT DOCUMENTS

| | | | | |
|---|---|---|---|---|
| 3,555,912 A * | 1/1971 | Lowell | ............... | G01N 15/0893 73/865.5 |
| 3,707,870 A * | 1/1973 | Herve | ............... | G01N 15/0893 73/38 |
| 3,732,736 A * | 5/1973 | Glaude | ................... | G01N 7/02 73/865.5 |
| 3,771,367 A * | 11/1973 | Lowell | ............... | G01N 15/0893 73/865.5 |
| 3,850,040 A * | 11/1974 | Orr, Jr. | ............... | G01N 15/0893 73/865.5 |
| 3,934,117 A * | 1/1976 | Schladitz | ................ | F24H 1/105 392/488 |
| 4,304,719 A * | 12/1981 | Wynne | ................... | C07F 5/003 252/501.1 |
| 4,332,290 A * | 6/1982 | Skala | ................... | F24H 7/0433 165/10 |
| 4,489,593 A * | 12/1984 | Pieters | ............... | G01N 15/0893 73/38 |
| 4,528,850 A * | 7/1985 | Witier | ............... | G01N 15/0893 73/865.5 |
| 4,560,288 A * | 12/1985 | Nara | ....................... | G01K 5/32 374/176 |
| 4,566,326 A * | 1/1986 | Lowell | ............... | G01N 15/0893 73/38 |
| 4,693,124 A * | 9/1987 | Killip | ....................... | B01L 7/00 62/373 |
| 4,762,010 A * | 8/1988 | Borghard | ........... | G01N 15/0893 73/38 |
| 4,872,353 A * | 10/1989 | Orr, Jr. | ................... | G01N 15/04 73/864.85 |
| 4,972,730 A * | 11/1990 | Camp | ................ | G01N 15/0893 73/865.5 |
| RE33,567 E | 4/1991 | Killip | | |
| 5,058,442 A * | 10/1991 | Yamanaka | ......... | G01N 15/0893 73/38 |
| 5,092,183 A * | 3/1992 | Leichnitz | .................. | F25D 7/00 422/83 |
| 5,109,716 A * | 5/1992 | Ito | ....................... | G01N 15/0893 73/38 |
| 5,133,219 A * | 7/1992 | Camp | ................ | G01N 15/0893 73/865.5 |
| 5,228,703 A * | 7/1993 | White | ..................... | F16J 15/022 250/352 |
| 5,235,184 A * | 8/1993 | Paulson | ................ | F25D 19/006 250/238 |
| 5,237,836 A * | 8/1993 | Byrne | ....................... | F25D 3/10 165/104.21 |
| 5,239,482 A * | 8/1993 | Ajot | ................... | G01N 15/0893 702/30 |
| 5,360,743 A * | 11/1994 | Lowell | ............... | G01N 15/0893 436/5 |
| 5,408,864 A * | 4/1995 | Wenman | ................ | G01N 15/08 73/38 |
| 5,591,897 A * | 1/1997 | Nakamura | ......... | G01N 15/0893 73/38 |
| 5,637,810 A * | 6/1997 | Conner, Jr. | ........ | G01N 15/0893 73/38 |
| 5,646,335 A * | 7/1997 | Wenman | ................ | G01N 15/08 73/38 |
| 5,744,699 A * | 4/1998 | Suzuki | ............... | G01N 15/0893 73/38 |
| 5,895,841 A * | 4/1999 | Lowell | ............... | G01N 15/0893 73/38 |
| 6,422,063 B1 * | 7/2002 | Anantheswaran | .......................... | G01N 15/0826 73/38 |
| 6,595,036 B1 * | 7/2003 | Nakai | ................ | G01N 15/0893 422/69 |
| 7,429,358 B1 * | 9/2008 | Gross | ....................... | G01N 7/02 422/50 |
| 7,850,918 B2 * | 12/2010 | Gross | ....................... | G01N 7/04 422/83 |
| 8,739,603 B2 * | 6/2014 | Micklash, II | ............ | G01N 7/04 73/31.04 |
| 9,784,637 B2 * | 10/2017 | Endo | .................... | G01M 3/2846 |
| 2007/0092974 A1 * | 4/2007 | Swenson | ............. | G01N 15/088 436/164 |
| 2013/0011925 A1 * | 1/2013 | Gilar | ....................... | C07K 1/36 436/87 |

OTHER PUBLICATIONS

Micromeritics ASAP 2020 Plus: Accelerated Surface Area and Porosimetry System; Brochure# 202/42704/00; 2014.

Micromeritics Gemini VII 2390 Series Surface Area Analyzers; Brochure# 239/42700/00; 2016.

British Standards Institute, BS 4359: Part 1 "Determination of the Specific Surface Area of Powders—Part 1 Recommendations for Gas Absorption (BET) Methods"; 1984.

Dollimore, D., et al., "The BET Method of Analysis of Gas Absorption Data and Its Relevance to the Calculation of Surface Aeas," Surface Technology, vol. 4, pp. 121-160 (1976).

Suzuki, Isao; "Temperature-Compensated, Differential Tensimeter for Measuring Gas Absorption by Low Surface Area Solids" Rev. Sci. Instrum. 53(7), Jul. 1982, pp. 1061-1066.

Branauer, Emmett and Teller; "Absorption of Gases in Multimolecular Layers"; (J. Am. Chem Soc., vol. 60, pp. 309-319); Feb. 1938.

Micromeritics TriStar II Series—Surface Area and Porosity Analyzers; Brochure# 303/42700/00; available prior to Dec. 2016.

Micromeritics ASAP 2050 Xtended Pressure Sorptinn Analyzer; available prior to Dec. 2016.

Micromeritics ASAP 2420 Accelerated Surface Area and Porosimetry System; available prior to Dec. 2016.

Micromeritics ASAP 2460 Accelerated Surface Area and Porosimetry System; Brochure# 246/42700/00; available prior to Dec. 2016.

* cited by examiner

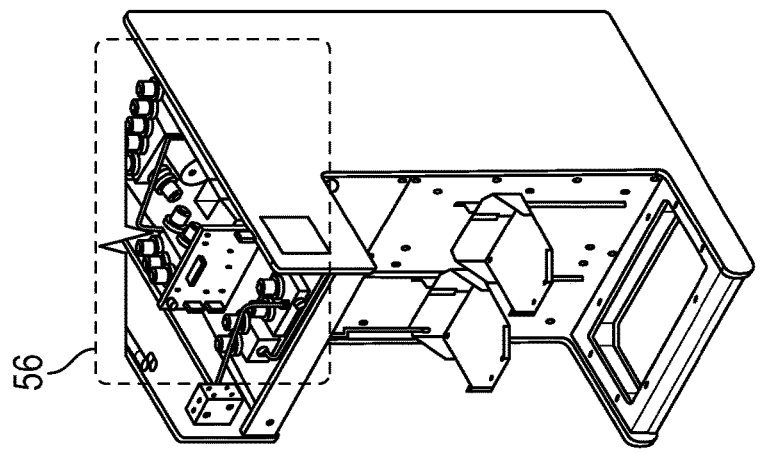
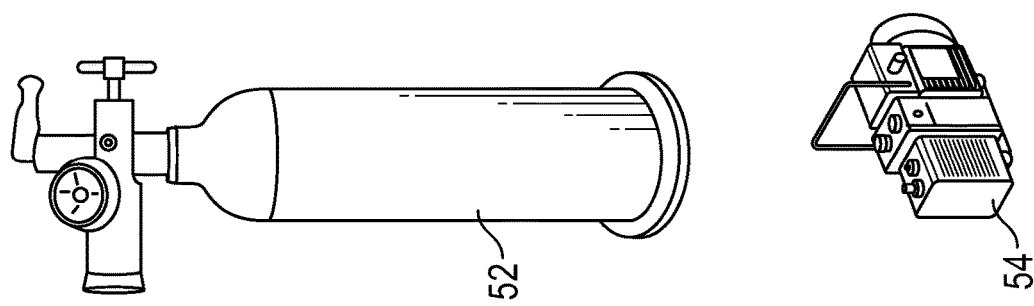
FIG. 1B
PRIOR ART
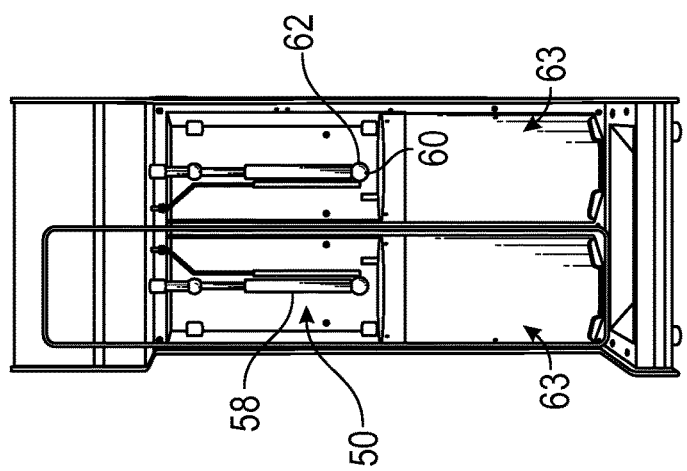

SYSTEMS AND METHODS FOR PROVIDING A PROFILE OF A MATERIAL PROPERTY USING MULTIPLE ANALYSIS STATIONS

CROSS-REFERENCE TO RELATED APPLICATIONS

The present application claims the benefit of U.S. Provisional Patent Application No. 62/434,233 filed Dec. 14, 2016.

INCORPORATION BY REFERENCE

The disclosure of U.S. Provisional Patent Application No. 62/434,233 filed Dec. 14, 2016, is hereby incorporated by reference as if presented herein in its entirety.

SUMMARY

In one aspect, the present disclosure is directed to a method and a system for combining/concatenating data collected from multiple analysis stations, which system provides final results faster than possible on a single analysis station.

In another aspect, the present disclosure is directed to a system for profiling a material property, and can include a plurality of measurement devices including at least a first measurement device, a second measurement device, and a controller in communication with the plurality of measurement devices to control the measurement devices to measure the material property. The first measurement device can measure a first segment of the material property, and the second measurement device can measure a second segment of the material property. The controller can be configured to scale the first segment of the material property to match at least one boundary of the second segment of the material property, and the controller can combine the first segment of the material property and the second segment of the material property to provide a profile of the material property.

In another aspect, the present disclosure can be directed to a method for profiling a property of a material. The method can include receiving one or more target parameters for measuring the property, dividing the target parameters into a plurality of segments, and assigning each segment of the plurality of segments to a measurement device of a plurality of measurement devices. The method further can include measuring at least one aspect of the property based at least in part on the assigned segment of the plurality of segments. Upon measurement of the at least one aspect of the material property, the method can include scaling the at least one aspect measured by each of the plurality of measurement devices, and combining the at least one aspect of the property measured by each of the plurality of measurement devices to generate an experimental profile of the property.

In another aspect, the present disclosure is directed to a measurement system for profiling a property of a selected material. The system can include a plurality of analysis stations and one or more controllers in communication with the plurality of analysis stations. The analysis stations can each have one or more measurement devices configured to measure or otherwise determine a selected material property. The controller can include a processor, which, among other things, can receive one or more target parameters for measuring the selected material property. The target parameters can be divided into a plurality of segments either by an operator or by the controller. Each segment of the plurality of segments can be assigned to an analysis station of the plurality of analysis stations, and the measurement device(s) of each analysis station can measure at least one aspect of the selected material property based on the analysis station's assigned segment. The processor of the controller can scale the aspects of the selected material property measured at each of the analysis stations. In one example, the processor matches one or more boundaries of the measured aspects of the selected material property. The processor can combine the scaled aspects of the selected material property measured at each analysis station, and the processor can generate a measurement or experimental profile of the selected property based at least in part on the scaled and combined aspects. The measurement/experimental profile can, for example, include a full isotherm report for the selected material, and the target parameters can, for example, include a plurality of pressures for measuring adsorption or desorption of the selected material. The at least one aspect of the material can include, for example, an adsorption or desorption data point of the selected material at one of the plurality of pressures.

In another aspect, the present disclosure is directed to a method and system for producing an isotherm report using a series of analysis stations. For example, adsorption and, optionally, desorption data can be collected for a sample that has been divided into multiple sample tubes, so the tubes can be analyzed on different/distinct analysis stations. Each station collects data for different segments of an isotherm, and the isotherm data from each of the stations can be concatenated to produce a single, full isotherm in less time than for an analysis performed by a single station to arrive at a full isotherm.

These and other advantages and aspects of the embodiments of the disclosure will become apparent and more readily appreciated from the following detailed description of the embodiments and the claims, taken in conjunction with the accompanying drawings. Moreover, it is to be understood that both the foregoing summary of the disclosure and the following detailed description are exemplary and intended to provide further explanation without limiting the scope of the disclosure as claimed.

BRIEF DESCRIPTION OF THE DRAWINGS

The accompanying drawings, which are included to provide a further understanding of the embodiments of the present disclosure, are incorporated in and constitute a part of this specification, illustrate embodiments of the invention, and together with the detailed description, serve to explain the principles of the embodiments discussed herein. No attempt is made to show structural details of this disclosure in more detail than may be necessary for a fundamental understanding of the exemplary embodiments discussed herein and the various ways in which they may be practiced.

FIGS. 1A-C respectively show an example measurement system, components of an example analysis station, and a schematic drawing of an example analysis station according to principles of the present disclosure.

DETAILED DESCRIPTION

Figure 1A:
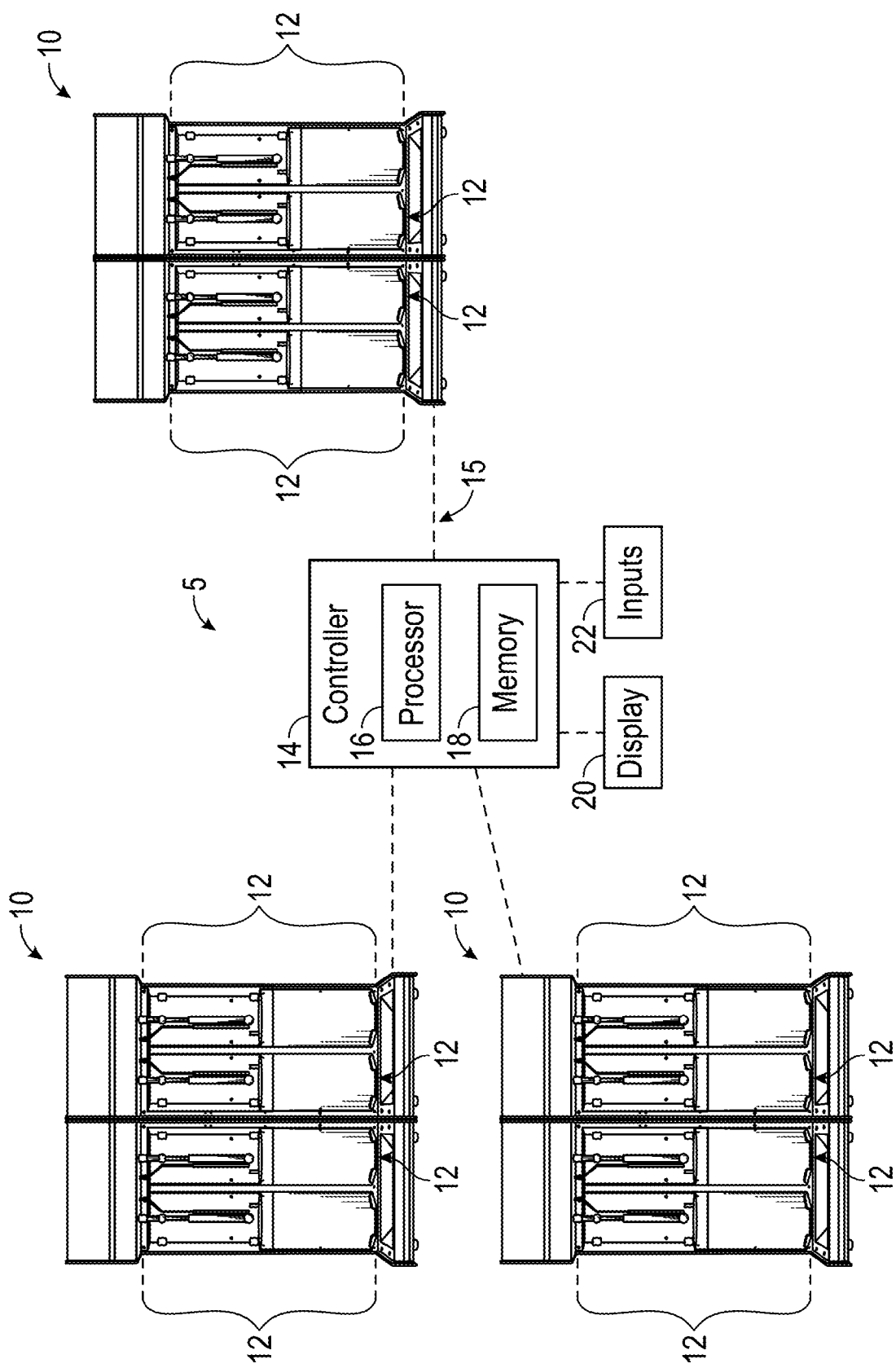
Figure 1C:
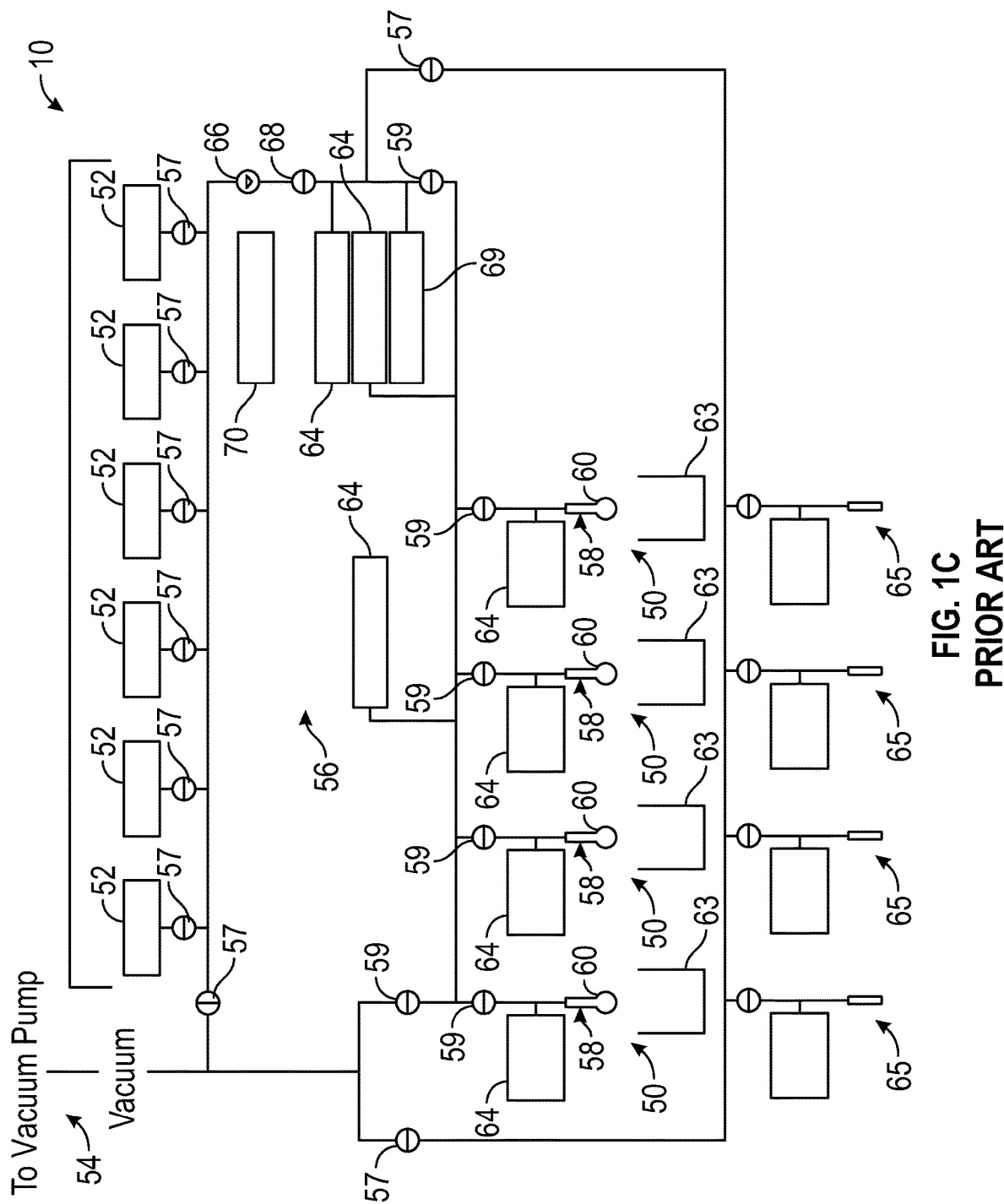

FIG. 1A shows an exemplary measurement system 5 that includes a plurality of analysis stations 10. Each analysis station 10 comprises one or more measurement devices 12 configured to measure or otherwise obtain at least one aspect of a selected material property. FIGS. 1B and 1C show an exemplary analysis station 10. The analysis station 10 can include or comprise a surface area or a surface area and porosity instrument, such as, for example, ASAP 2420, ASAP 2460, ASAP 2020, Tristar 3020, Tristar 3030 of Micromeritics Instrument Corporation of Norcross, Ga., or another suitable physisorption or chemisorption instrument/ system, such as, for example, a 3Flex of Micromeritics Instrument Corporation.

The analysis stations 10 can be connected to, or otherwise in communication with, a controller 14. Controller 14 can include a Central Processing Unit (CPU), such as a desktop computer, laptop or server, and/or the controller 14 can include any suitable device such as a tablet, mobile phone, personal data assistant or other suitable mobile device, without departing from this disclosure. The controller 14 includes a processor 16, or other suitable physical computing components, and a memory 18. The processor 16 is operable to access memory 18 and carry out one or more programs or instructions, which programs and instructions can be stored therein. The memory 18 can include Random Access Memory (RAM), Read Only Memory (ROM), or other suitable non-transitory computer readable medium. The controller 14 is operable to receive measurement data from the analysis stations 10. The measurement data can include data related to the aspect of the selected material measured by the one or more measurement devices 12 of each analysis station 10. The controller 14 can be in direct communication with each of the analysis stations 10, or in the alternative, the controller 14 can be in communication with a network 15 that is in communication with each of the analysis stations 10. The controller 14 further may be connected to or otherwise in communication with a display 20 and/or one or more inputs 22, such as a keyboard, mouse, touchscreen, voice recognition device, or other suitable input.

Figure 2:
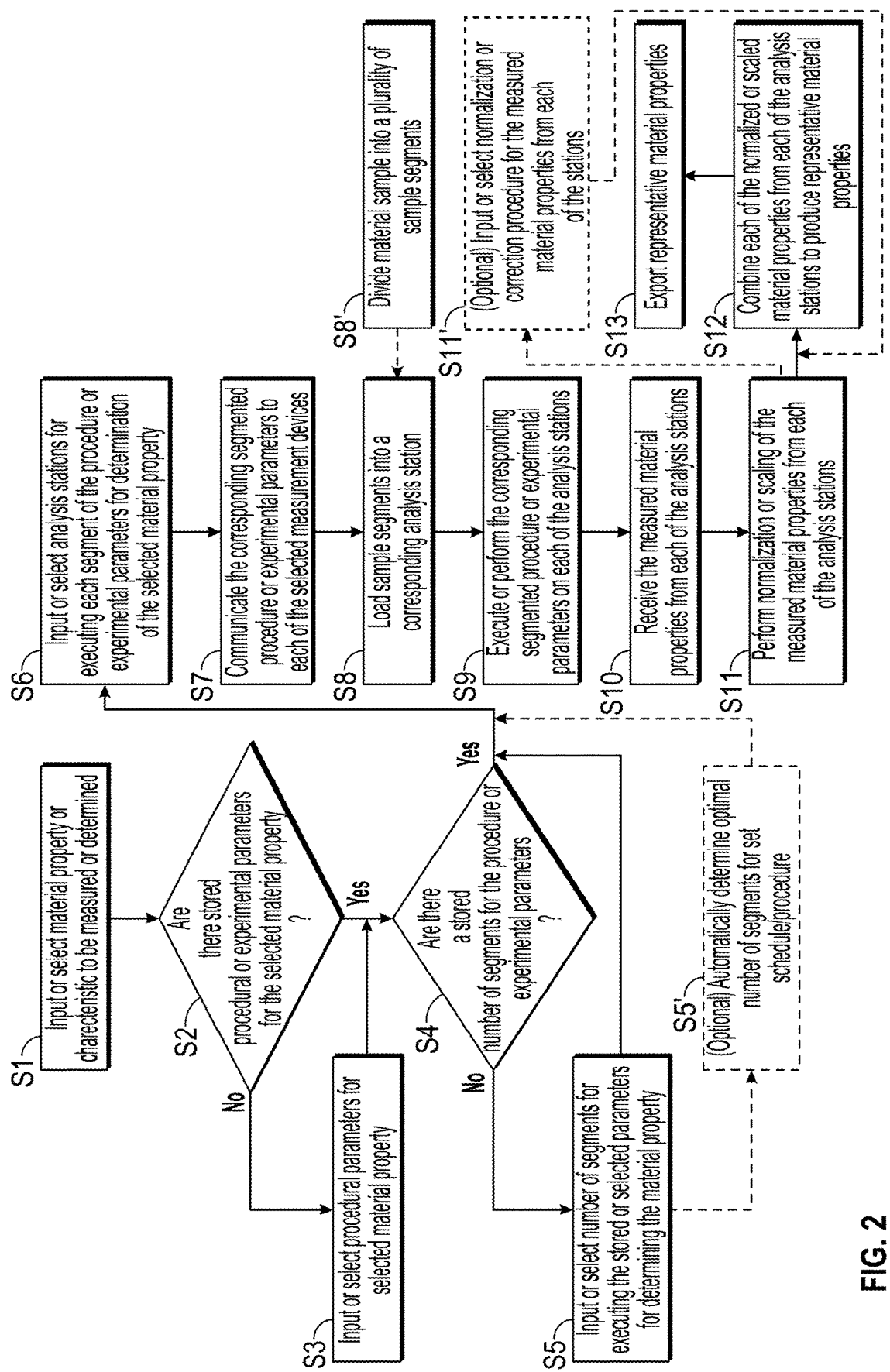
FIG. 2 shows a flow chart for measuring or otherwise determining a profile of a selected material property using multiple analysis stations according to one aspect of the present disclosure.
Figure 3:
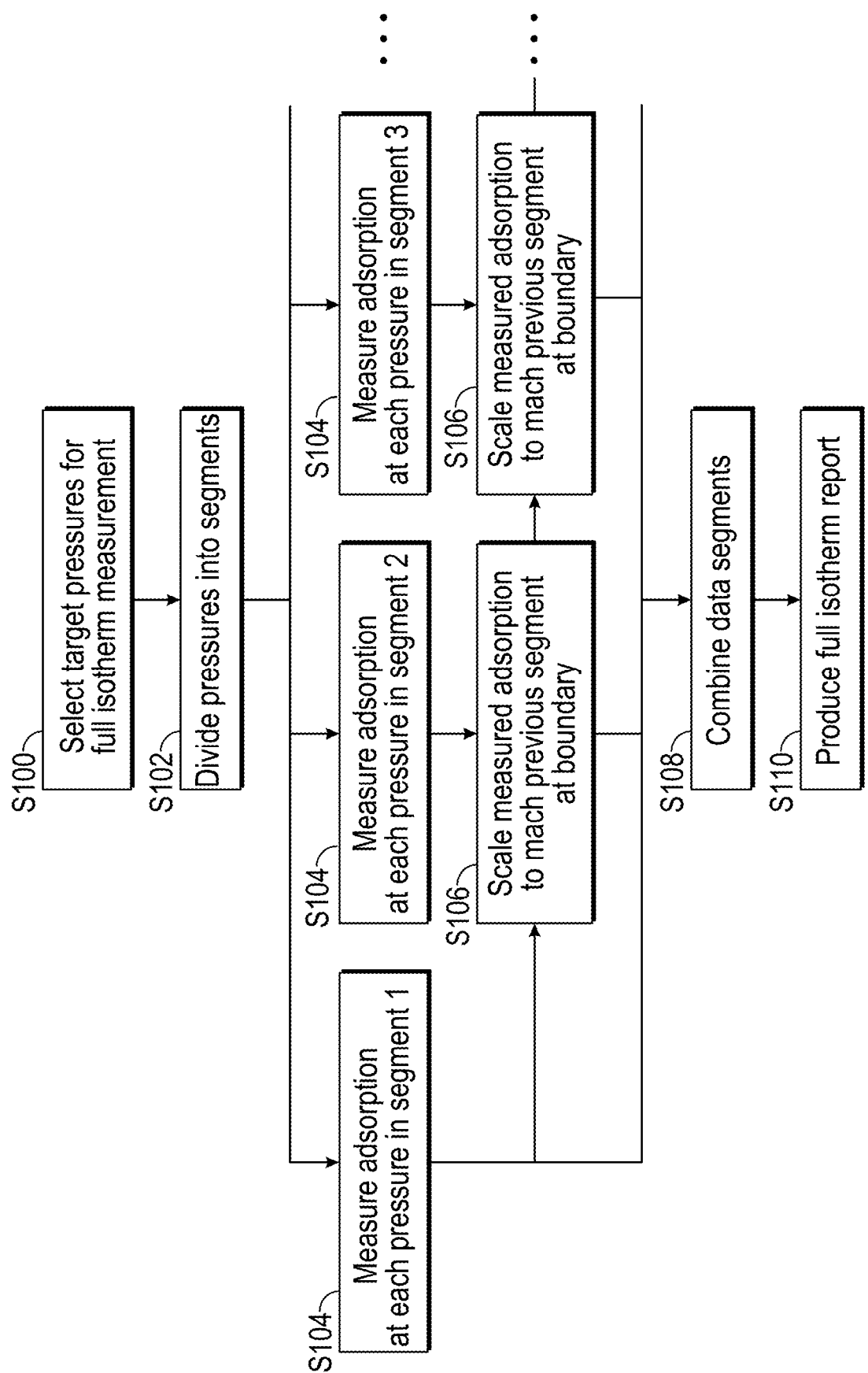
FIG. 3 shows a flow chart for producing an isotherm report using multiple analysis stations.

Measurement system 5 is operable to profile a material property of a selected material, as generally shown in FIGS. 2 and 3. For example, procedural or experimental target parameters for determining the selected material property are selected, and the selected parameters are divided into a plurality of segments. The plurality of segments are carried out on divided segments or aliquots of a sample of the selected material at selected analysis stations 10 of the plurality of analysis stations 10 to determine at least one aspect of the material property. The measured aspects of the material property measured/determined at each selected analysis station 10 are communicated to the controller 14, and the processor 16 can concatenate or otherwise combine the measured/determined aspects to provide a full profile of the material property.

FIG. 2 shows an exemplary process of operation of an analysis station. In FIG. 2, a user inputs or selects a material property or characteristic, e.g. morphological characteristic or other suitable characteristic, to be measured by the measurement system (shown at S1). For example, the user can input a material property into the one or more inputs 22 of the controller 14, or the user can select a material property from a list of material properties that can be shown on the display 20. In another example, the property or characteristic measured is determined by analysis parameters, such as, for example, a target pressure, and/or by the type of data analysis performed. The display 20 may show a list or other grouping of analysis parameters, or types of data analysis to be performed, that can be selected by the user or the user can input analysis parameters, or types of data analysis to be performed, into input(s) 22.

Upon input or selection of the material property or characteristic to be measured, the processor 16 can determine whether procedural or experimental analysis parameters for measuring or otherwise determining the stored material property are stored in the memory 18 (shown at S2). If parameters are not stored in the memory, the user can input or otherwise select particular procedural/experimental analysis parameters for measuring the material property using one or more inputs 22 of the controller 14 (shown at S3).

FIG. 2 further shows that, after the processor 16 has obtained the procedural or experimental parameters, the processor 16 determines whether the memory 18 contains information on dividing the inputted/received parameters into segments, or whether a stored number of segments for the procedure or experimental parameters is contained in the memory 18 (S4). If the memory fails to contain information for dividing the parameters into segments, the user may input or select, e.g., into input(s) 22, a prescribed number of segments for dividing the procedural or experimental procedures (shown at S5). Optionally, the processor 16 may automatically determine an optimal number of segments for dividing the set experimental/procedure parameters based on the material property to be measured, the specific experimental or procedural parameters, or other suitable factors (shown at S5').

Upon retrieval, selection, or determination of the number of segments for the experimental or procedural parameters, the processor 16 selects an available analysis station or stations 10 for executing each segment of the procedure or experimental parameters (shown at S6). A user further may be able to select or input specific analysis stations 10 for carrying out each segment of the schedule or procedure for measuring the selected material property. The processor 16 may communicate each segment of the plurality of segments to a corresponding analysis station 10 of the plurality of analysis stations 10 (shown at S7). Alternatively, a user may input information related to each of the segments into one or more inputs of the corresponding analysis stations 10.

A material sample is divided or segregated into a plurality of segments or aliquots (shown at S8'), and the segments can be loaded into the selected analysis station (shown at S8). Each analysis station 10 can execute or perform a corresponding segment of the parameters using one or more of the measurement devices 12 to measure at least one aspect of the selected material property of the sample loaded in the measurement device 12 (shown at S9).

The processor 16 receives each measured aspect of the material property from each of the analysis stations (shown at S10). For example, each of the analysis stations 10 can communicate the corresponding measured property to the processor 16, such as over the network. Optionally, a user can obtain data related to the measured property from each of the analysis stations 10 and input or otherwise communicate this data to the controller 14. The processor 16 normalizes or scales the measured aspects received from the analysis stations 10. For example, scaling may comprise matching one or more boundaries of the measured aspects so the boundaries of the measured aspects generally match (S11). The user can input or select a specific normalization or correction procedure such as from a list or other grouping of procedures shown on the display 20 (shown at S11').

The processor 16 can combine the scaled or normalized material properties to provide representative material properties or a profile of the selected material property (shown at S12). The processor 16 may then export the representative material properties or display the material properties on the display 20 (shown at S13).

According to principles of the present disclosure, the measurement system and method can be used to measure morphological characteristics of solids, e.g., such as catalysts, catalyst supports, pigments, clays, minerals, pharmaceuticals, or other composite materials. One example of a morphological characteristic includes a surface area of a sample material, which can be measured or determined using gas adsorption or desorption techniques, where the surface of the solid, e.g., the adsorbent, can be characterized as being covered by a monolayer of closely packed molecules of an adsorbed gas. For example, the amount of adsorbate which forms the monolayer can be determined, and an area covered by the monolayer can be calculated from the product of the number of molecules in the monolayer and the cross sectional area of each molecule using a mathematical model. Some mathematical models include using an adsorption isotherm of the adsorbate to determining the amount of adsorbate in the monolayer. One such mathematical model includes the BET equation:

$$\frac{1}{v[(p_0/p)-1]} = \frac{c-1}{v_m c}\left(\frac{p}{p_0}\right) + \frac{1}{v_m c},$$

where $p$ is the equilibrium pressure of adsorbates at the temperature of adsorption, $p_0$ is the saturation pressure of adsorbates at the temperature of adsorption, $v$ is the adsorbed gas quantity, $v_m$ is the monolayer adsorbed gas quantity, and $c$ is related to the heat of adsorption. The BET equation generally provides a relation between relative pressure and amount of gas adsorbed, and can be derived by assuming a particular model that describes how gas molecules form adsorbed layers on a solid material. The equation is generally effective for use with experimental data for a wide range of materials when relative pressure is in the range of about 0.1 to about 0.3. The BET equation can be arranged so that the amount of gas in monolayer that is directly in contact with the adsorbent can be found if pressure and amount adsorbed is known. Surface area is the number of molecules in the monolayer multiplied by the cross-sectional area of one adsorbate molecule.

The adsorption isotherm can include a plot of the amount of the adsorbate adsorbed on a solid adsorbent against either the relative pressure or the equilibrium pressure of the adsorbate at a constant temperature. Adsorption isotherms can be determined by measuring the sample pressure and determining the amount of adsorbate adsorbed either with a volumetric method or a gravimetric method, though another suitable method can be employed without departing from the present disclosure. Volumetric techniques can include static or fully equilibrated, continuous flow or quasi-equilibrated, and dynamic or chromatographic techniques. Volumetric methods can employ a selected adsorptive at a prescribed temperature for adsorption. The temperature of the adsorptive can be achieved by means of a liquid nitrogen ($LN_2$) bath in a dewar open to the atmosphere, and the adsorptive can be cooled to a temperature of about 70 Kelvin ("K") to about 80K, such as 77K.

As shown in FIGS. 1B and 1C, the analysis stations 10 can include a surface area and porosity system operable to measure material parameters using adsorption and/or desorption techniques, for example, to determine isotherms. FIGS. 1B and 1C show the analysis station(s) 10 includes, for example, a plurality of volumetric devices 50, one or more gas storage units 52, a vacuum unit 54, and a doser unit or other suitable volumetric measuring device 56. As generally shown in FIG. 1C, the gas storage unit 52 and the vacuum unit 54 typically are connected to the doser unit 56 by one or more valves 57. Additionally, the doser unit 56 typically is connected to the volumetric devices 50 by valves 59 (FIG. 1C). The volumetric devices 50 generally include a plurality of sample units 58 each including a sample tube having a chamber 60 sized, dimensioned, and/or configured to receive a material sample 62 to be tested. In one example, the volumetric devices 50 additionally can include a dewar 63 that receives a cryogen, for example, liquid nitrogen ($LN_2$), to control the temperature of the adsorptive; however, in another example, the volumetric devices 50 can include a CryoStat or other suitable device/mechanism for controlling temperatures. The analysis station(s) 10 further can include a plurality of saturation pressure tubes 65 corresponding to each of the volumetric devices 50. The doser unit 56 further includes one or more pressure transducers or other suitable pressure sensors 64, a proportional valve 66, a solenoid valve 68, and one or more vacuum gauges 69. The proportional valve 66 is operable to control a gas flow rate from the gas storage unit(s) 52 and/or the vacuum unit 54, and the solenoid valve 68 is operable to stop or start gas flow from the gas storage unit(s) 52 and/or the vacuum unit 54. The vacuum unit 54 typically includes a vacuum pump or other suitable vacuum source. The analysis station(s) 10 additionally includes a manifold temperature sensor 70.

In operation, the doser 56 and/or sample units 58 can be evacuated, for example, using vacuum unit 54, and the evacuated doser 56 can be sealed off from the evacuated sample chamber 60, for example, by closing the solenoid valve 68, though the doser 56 can be sealed off by closing valves 57 and/or 59. Nitrogen ($N_2$), or other suitable gas, for example, helium (He) or krypton (Kr), can be fed into the doser unit 56 from the gas storage unit 52 to a target pressure, for example, by opening valves 57, or solenoid valve 68. The valves 57, or the solenoid valve 68, then can be closed to seal the doser unit 56, and a pressure of nitrogen ($N_2$) in the doser unit 56 can be measured using one or more of the pressure transducers 64. When a constant pressure is achieved in the doser unit 56, the valves 59 separating the sample chambers 60 and doser unit 56 can be opened to allow the adsorptive, typically $N_2$, in the doser unit 56 to expand into the sample chamber 60.

The doser unit 56 has a Volume V1, and the chambers 60 of the sample units 58 have a Volume V2. The sample chamber 60 and doser unit 56 together define a Volume V3 (e.g., V1+V2). When the pressure in V3 is constant, which is indicative of adsorption equilibrium, the pressure can be measured using one or more of the pressure transducers 64. The equilibrium pressure can be used to calculate the total number of moles of $N_2$ that remains in the gas phase. The number of moles of $N_2$ adsorbed on each sample can be equal to the number of moles of $N_2$ initially present in volume of the doser V1, plus the number of moles of $N_2$ in each sample chamber defining Volume V2 (the number of moles in Volume V1 for the initial run is generally zero, but increases with each successive run), less the number of moles of gaseous $N_2$ in Volume V3, after equilibrium. The combined data of the amount of $N_2$ adsorbed at a particular equilibrium pressure may constitute a single point on the adsorption isotherm.

The above-described procedure can be repeated to obtain additional points on the adsorption isotherm. Each successive dose increases the pressure in the sample chamber(s) until, at approximately atmospheric pressure, the sample becomes completely saturated with condensed $N_2$. At the point of saturation, the majority of the $N_2$ condensation occurs on the sample contained in the sample holder. Heuristics generally can be used predict the amount gas that will be adsorbed at each subsequent target pressure based at least in part on data collected during the current analysis of the samples. Additionally, or in the alternative, data collected from an earlier/previous analysis can be used to determine the amount adsorbed at a subsequent pressure target. Generally, for example, surface area determinations involve determining up to about 10 data points on the adsorption isotherm. However, when detailed analysis of both the smallest pores and the largest pores of a material is required, hundreds of data points can be collected.

As shown in FIG. 3, a user can select target pressures for a full isotherm measurement (shown at S100), and the selected target pressures can be divided into a plurality of segments for measuring adsorption at a prescribed analysis station 10 of the plurality of analysis stations 10 (shown at S102). In one example, the target pressures may be divided based on previously collected data to minimize analysis time. A sample of the material is divided into multiple aliquots or segments. Each aliquot or segment is inserted into a sample unit or vessel 72. Each sample vessel 72 is installed or loaded into separate sample ports or stations, e.g. sample chamber 60, of a measurement device 10 (volumetric device 50) of the analysis stations 10. Each measurement/volumetric device 10/50 is operable to collect data for a different part or segment of a full isotherm. Each measurement/volumetric device 10/50 can be used to measure adsorption of a corresponding sample loaded at an assigned pressure segment (shown at S104).

Figure 4:
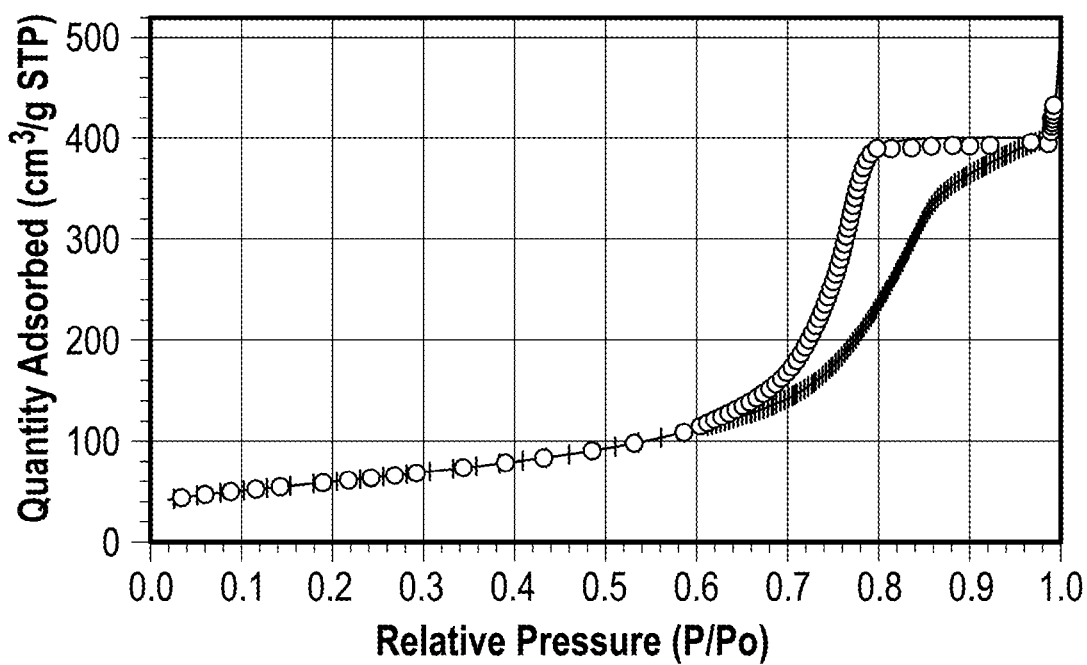
FIG. 4 shows a full isotherm collected on a single exemplary sample.

FIG. 4 shows a full isotherm collected on a single sample. Measurement or development of a full isotherm using a single sample may require a significant amount of time, e.g., up to about 30 hours or longer. The time required for measurement can be longer if the materials required, e.g., $LN_2$, are exhausted and/or must be refilled during measurement of the isotherm. Further, as such tests typically run multiple hours or days, tests can be interrupted for any number of reasons, such as, for example, power outages, which can prolong the time required to obtain results or potentially introduce errors into the measurements. Developing isotherms from a plurality of samples using principles of the present disclosure can sufficiently reduce the time needed to develop a full isotherm. Measurement of an isotherm using the systems and methods disclosed herein generally requires less time, for example, only about 9 hours and each of the segments may be measured without requiring refill of measurement materials, e.g. $LN_2$.

Figure 5A:
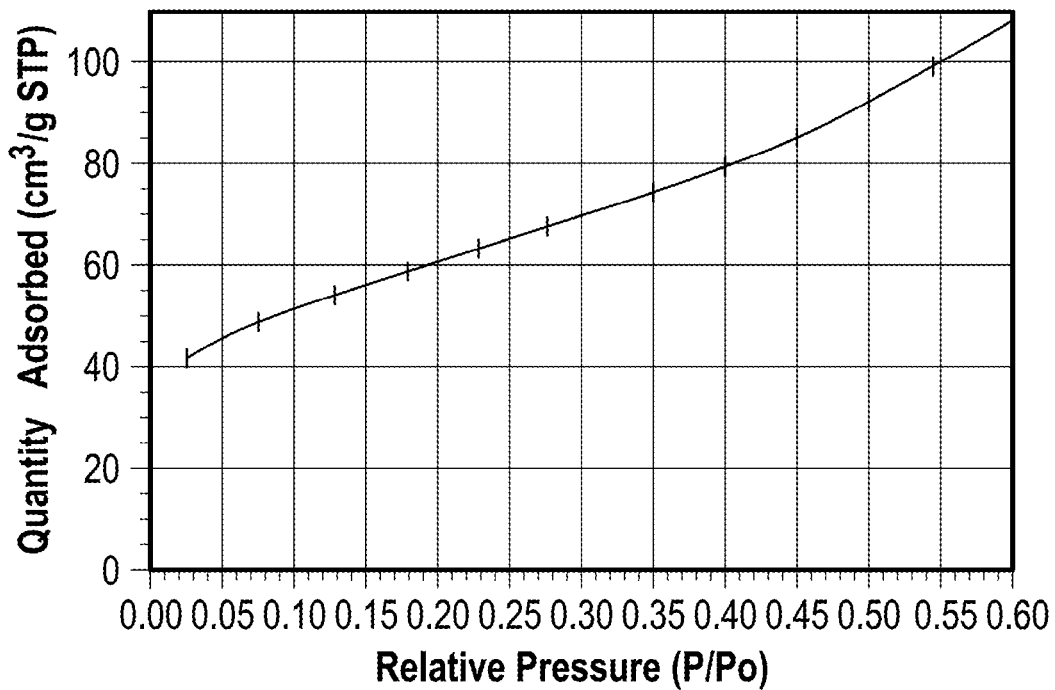
FIGS. 5A-C show partial isotherms determined according to principles of the present disclosure.
Figure 5B:
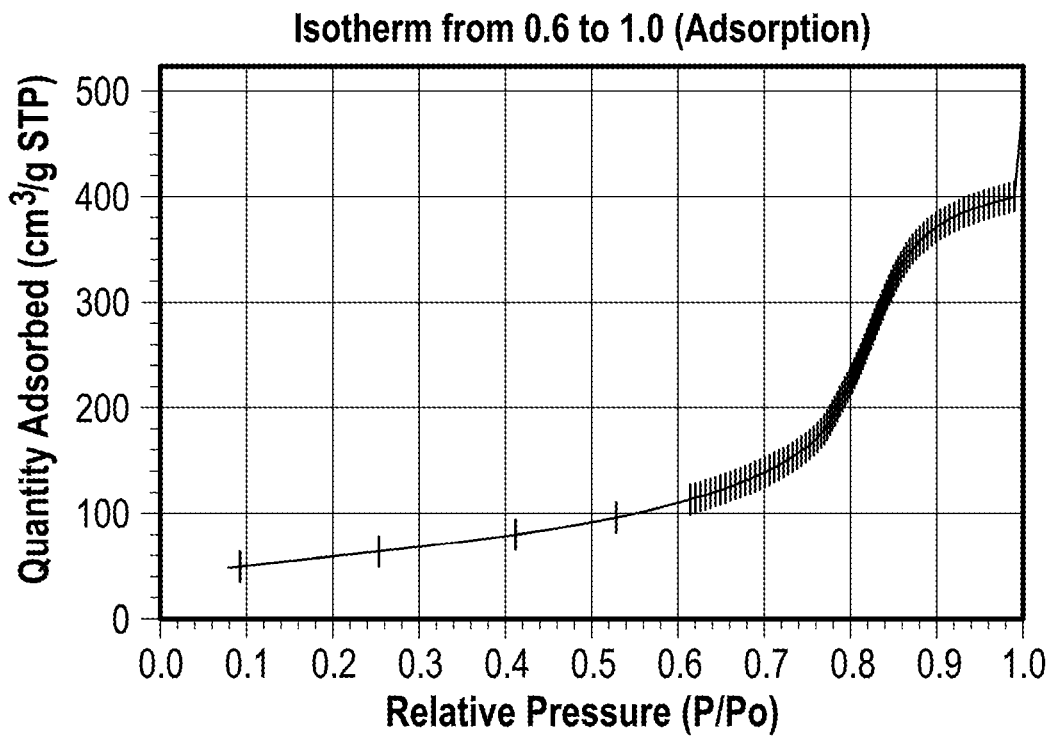
Figure 5C:
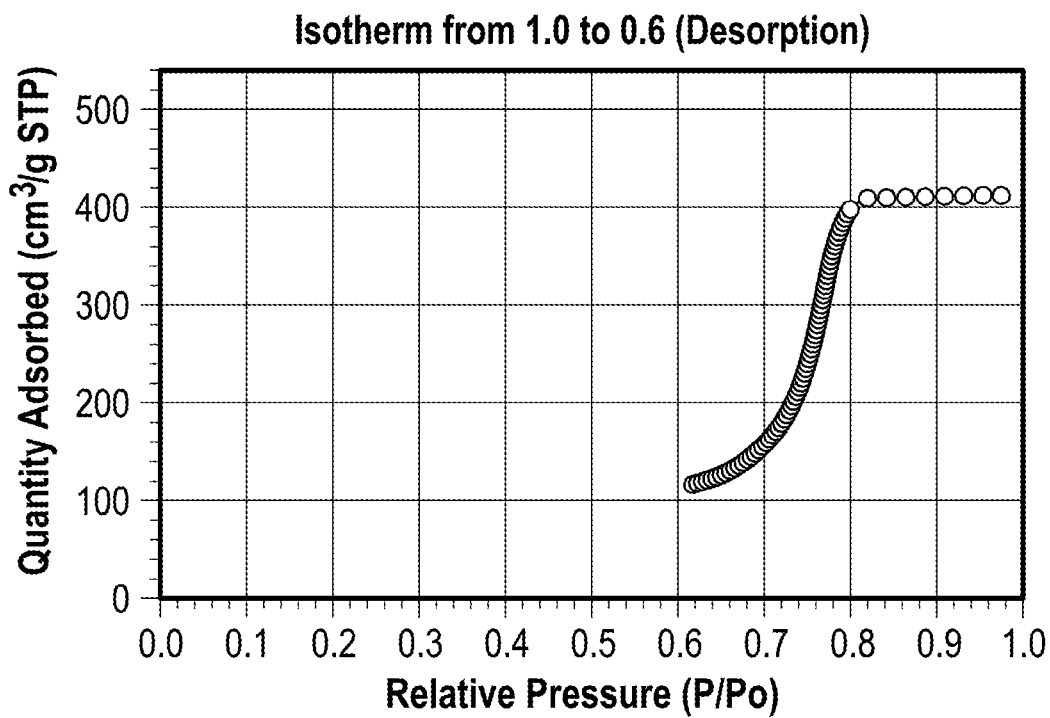

FIGS. 5A-C show a series of partial isotherms at different relative pressure ranges, e.g., 0 to 0.6 (FIG. 5A), 0.6 to 1.0 (FIG. 5B) and 1.0 to 0.6 (FIG. 5C). After the adsorption at each pressure segment is measured, the measured adsorptions are scaled or normalized to match substantially at one or more boundaries (S106). For example, the partial isotherm shown in FIG. 5A can be scaled such that one or more boundaries shown in FIG. 5A substantially matches one or more boundaries of the partial isotherm in FIG. 5B, and the partial isotherm shown in FIG. 5B can be scaled such that one or more boundaries shown in FIG. 5B substantially matches one or more boundaries of the partial isotherm in FIG. 5C.

Under ideal conditions, each measurement device 12 or volumetric device 50 would provide exactly the same isotherm. However, variations between measurement devices 12 or volumetric devices 50, and between repeated measurements on a given measurement device 12 or volumetric device 50 may occur. The variations may result in minor discrepancies where the isotherm segments meet, e.g., at one or more boundaries. The discrepancies can cause artifacts in the reported results. For example, the discrepancies can produce peaks in a pore size distribution graph that could be mistaken as properties of the material. The largest variations generally result in a vertical scaling of the isotherm, and thus, the second segment of the isotherm (FIG. 5B) can be vertically scaled so that the data points in the first (FIG. 5A) and second (FIG. 5B) segments lie on a smooth curve. The third segment (FIG. 5C) can then be scaled to match the second segment (FIG. 5B) and so on.

In one example, points outside of each segment's pressure range can be discarded, optionally. For example, intermediate points between the different target pressures can be removed. The widely spaced points at the beginning of the isotherm shown in FIG. 5B include examples of points that could be discarded.

Figure 6:
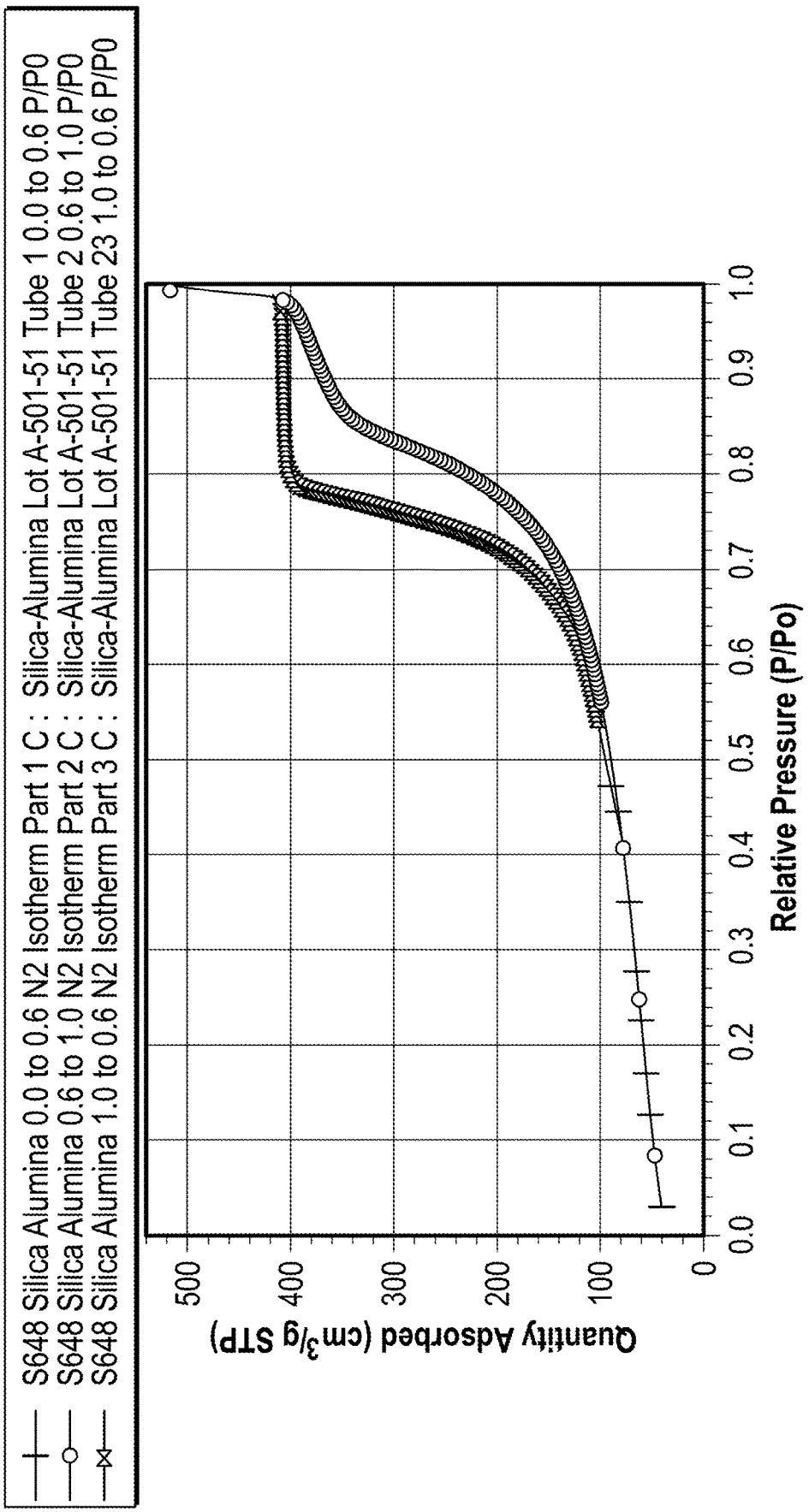
FIG. 6 shows an isotherm generated based on the partial isotherms of FIGS. 5A-C.

The scaled partial isotherms can be combined to produce a full isotherm, e.g., as generally shown in FIG. 6. For example, the adsorption data points (pressure and corresponding amount adsorbed) from all segments can be combined into a table or other grouping, e.g., in order of increasing pressure. Then, the desorption data from all segments, ordered by descending pressure, can be appended. A single table listing or grouping of pressures (for example, in ascending and descending order) and amount adsorbed can then be produced. Plotting pressure on the x-axis and amount adsorbed on the y-axis provides the graph shown in FIG. 6.

The foregoing description generally illustrates and describes various embodiments of the present disclosure. It will, however, be understood by those skilled in the art that various changes and modifications can be made to the above-discussed construction of the present invention without departing from the spirit and scope of the invention as disclosed herein, and that it is intended that all matter contained in the above description or shown in the accompanying drawings shall be interpreted as being illustrative, and not to be taken in a limiting sense. Furthermore, the scope of the present disclosure shall be construed to cover various modifications, combinations, additions, alterations, etc., above and to the above-described embodiments, which shall be considered to be within the scope of the present disclosure. Accordingly, various features and characteristics of the present disclosure as discussed herein may be selectively interchanged and applied to other illustrated and non-illustrated embodiments of the disclosure, and numerous variations, modifications, and additions further can be made thereto without departing from the spirit and scope of the present disclosure as set forth in the appended claims.

What is claimed is:

1. A system for profiling a material property, comprising:
   a plurality of measurement devices configured to measure at least a portion of the material property; and a controller comprising at least one processor in communication with one or more of the plurality of measurement devices;

wherein at least one measurement device of the plurality of measurement devices measures at least one segment of the material property, and at least one additional measurement device of the plurality of measurement devices measures at least one additional segment of the material property, and wherein the processor combines the at least one segment and the at least one additional segment to provide at least a partial profile of the material property.

2. The system of claim 1, wherein the processor scales the at least one segment to at least partially match a boundary of the at least one additional segment.

3. The system of claim 1, wherein the profile is an isotherm.

4. The system of claim 1, wherein one or more of the plurality of measurement devices comprises a surface area and porosity system configured to measure the material property using adsorption and/or desorption.

5. The system of claim 4, wherein the surface area and porosity system comprises one or more sample units having a chamber to receive a portion of a sample of the material.

6. The system of claim 5, wherein the surface area and porosity system further comprises:

a gas storage unit;

at least one vacuum unit; and at least one doser unit connected to at least one of the one or more sample units by at least one valve, wherein the doser unit and the at least one sample unit are evacuated using the at least one vacuum unit, wherein at least one fluid is fed into the evacuated doser unit from the gas storage unit, and wherein when a substantially constant pressure is reached in the doser unit, the valve is opened to allow the fluid to at least partially enter the chamber of the at least one sample unit.

7. A method for profiling a material property, comprising:

receiving one or more target parameters for measuring the material property;

dividing the target parameters into a plurality of segments;

assigning each segment of the plurality of segments to a measurement device of a plurality of measurement devices;

measuring a plurality of aspects of the material property with the corresponding measurement devices of the plurality of measurement devices assigned to each segment of the plurality of segments; and combining the plurality of aspects to generate at least a portion of an experimental profile of the material property.

8. The method of claim 7, further comprising:

normalizing or scaling one or more of the plurality of aspects.

9. The method of claim 8, wherein the normalizing or scaling comprises substantially matching at least a portion of a boundary of at least one aspect of the plurality of aspects with at least a portion of an additional boundary of at least one additional aspect of the plurality of aspects.

10. The method of claim 7, wherein the experimental profile is an isotherm.

11. The method of claim 7, wherein one or more of the plurality of measurement devices comprises a surface area and porosity system configured to measure the material property using adsorption and/or desorption.

12. The method of claim 11, wherein the surface area and porosity system comprises one or more sample units having a chamber to receive a portion of a sample of the material.

13. The method of claim 12, wherein the surface area and porosity system further comprises:

a gas storage unit;

at least one vacuum unit; and at least one doser unit connected to at least one of the one or more sample units by at least one valve, wherein the doser unit and the at least one sample unit are evacuated using the at least one vacuum unit, wherein at least one fluid is fed into the evacuated doser unit from the gas storage unit, and wherein when a substantially constant pressure is reached in the doser unit, the valve is opened to allow the fluid to at least partially enter the chamber of the at least one sample tube unit.

14. A measurement system, comprising:

a plurality of analysis stations each comprising one or more measurement devices; and a processor operable to:

receive target parameters for measuring a material property;

divide the target parameters into a plurality of segments;

assign each segment of the plurality of segments to an analysis station of the plurality of analysis stations;

instruct the plurality of analysis stations to activate the one or more measurement devices to measure a plurality of aspects of the material property based at least in part on the assigned segments; and combine the plurality of aspects to generate at least a portion of an experimental profile of the material property.

15. The measurement system of claim 14, wherein the processor is further operable to normalize or scale one or more of the plurality of aspects.

16. The measurement system of claim 15, wherein the scaling or normalizing comprises substantially matching at least a portion of a boundary of at least one aspect of the plurality of aspects with at least a portion of a boundary of at least one additional aspect of the plurality of aspects.

17. The measurement system of claim 14, wherein the experimental profile is an isotherm.

18. The measurement system of claim 14, wherein one or more of the plurality of analysis stations comprises a surface area and porosity system configured to measure the material property using adsorption and/or desorption.

19. The measurement system of claim 18, wherein the surface area and porosity system comprises one or more sample units having a chamber to receive a portion of a sample of the material.

20. The measurement system of claim 19, wherein the surface area and porosity system further comprises:

a gas storage unit;

at least one vacuum unit; and at least one doser unit connected to at least one of the one or more sample units by at least one valve, wherein the doser unit and the at least one sample unit are evacuated using the at least one vacuum unit, wherein at least one fluid is fed into the evacuated doser unit from the gas storage unit, and wherein when a substantially constant pressure is reached in the doser unit, the valve is opened to allow the fluid to at least partially enter the chamber of the at least one sample tube unit.

* * * * *